United States Patent [19]

Hofmeister et al.

[11] 4,081,537
[45] Mar. 28, 1978

[54] $\Delta^{15}$-STEROIDS AND PHARMACEUTICAL COMPOSITIONS THEREOF

[75] Inventors: Helmut Hofmeister; Rudolf Wiechert; Klaus Annen; Henry Laurent; Hermann Steinbeck, all of Berlin, Germany

[73] Assignee: Schering Aktiengesellschaft, Berlin and Bergkamen, Germany

[21] Appl. No.: 728,896

[22] Filed: Oct. 4, 1976

[30] Foreign Application Priority Data

| Oct. 10, 1975 | Germany | 2546062 |
|---|---|---|
| Aug. 12, 1976 | Germany | 2636407 |
| Aug. 12, 1976 | Germany | 2636404 |
| Aug. 12, 1976 | Germany | 2636405 |

[51] Int. Cl.² .......................... C07J 1/00; A61K 31/56
[52] U.S. Cl. ..................... 424/238; 424/241; 424/243; 424/240; 260/397.45; 260/239.55 R; 260/397.4; 260/397.5
[58] Field of Search ............................ 260/397.4, 397.5

[56] References Cited

U.S. PATENT DOCUMENTS

| 3,433,785 | 3/1969 | Manson et al. | 260/397.5 |
|---|---|---|---|
| 3,475,463 | 10/1969 | Phillips | 260/397.4 |
| 4,016,269 | 4/1977 | Hofmeister et al. | 260/239.55 |

Primary Examiner—Elbert L. Roberts
Attorney, Agent, or Firm—Millen & White

[57] ABSTRACT $\Delta^{15}$-Steroids of the formula

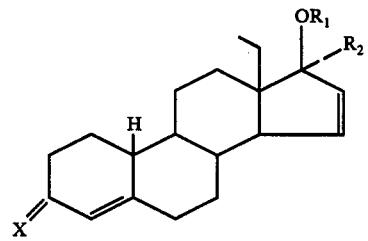

wherein $R_1$ is a hydrogen atom, trialkylsilyl or acyl; $R_2$ is ethynyl, chloroethynyl or propinyl; and X is an oxygen atom,

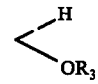

or $NOR_4$ wherein $R_3$ is a hydrogen atom or acyl and $R_4$ is a hydrogen atom, acyl, alkyl or tetrahydropyranyl, possess progestational and ovulation and nidation inhibiting activities.

53 Claims, No Drawings

$\Delta^{15}$-STEROIDS AND PHARMACEUTICAL COMPOSITIONS THEREOF

BACKGROUND OF THE INVENTION

This invention relates to $\Delta^{15}$-steroids.

SUMMARY OF THE INVENTION

In a composition aspect, this invention relates to $\Delta^{15}$-steroids of general Formula I

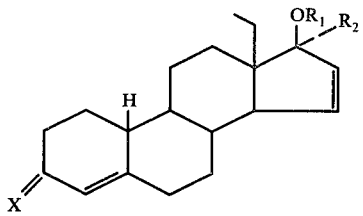

wherein $R_1$ is a hydrogen atom, trialkylsilyl or acyl; $R_2$ is ethynyl, chloroethynyl or propinyl; and X is an oxygen atom,

or $NOR_4$ wherein $R_3$ is a hydrogen atom or acyl and $R_4$ is a hydrogen atom, acyl, alkyl or tetrahydropyranyl.

In another composition aspect, this invention relates to pharmaceutical compositions comprising a compound of general Formula I.

In process aspects, this invention relates to methods of making and using compounds of general Formula I.

DETAILED DISCUSSION

Examples of compounds within the scope of Formula I are those wherein:
 a. X is an oxygen atom;
 b. X is $NOR_4$ wherein $R_4$ is H, alkanoyl of 2-8 carbon atoms, alkyl of 1-4 carbon atoms or cycloalkyl of 3-8 carbon atoms;
 c. X is

wherein $R_3$ is H or alkanoyl of 1-11 carbon atoms;
 d. $R_1$ is H, including each of the compounds of (a), (b) and (c);
 e. $R_1$ is trialkylsilyl, including each of the compounds of (a), (b) and (c);
 f. $R_1$ is alkanoyl of 1-11 carbon atoms, including each of the compounds of (a), (b) and (c);
 g. $R_2$ is ethynyl, including each of the compounds of (a), (b), (c), (d), (e) and (f);
 h. $R_2$ is chlorethinyl, including each of the compounds of (a), (b), (c), (d), (e) and (f);
 i. $R_2$ is propinyl, including each of the compounds of (a), (b), (c), (d), (e) and (f).

Examples of suitable $R_1$ and $R_3$ acyl groups are those of physiologically acceptable acids, preferably organic carboxylic and sulfonic acids of 1-16, especially 1-11 carbon atoms. Although acyl of alkanoic and alkanesulfonic acids are preferred, contemplated equivalents are acyl of all other carboxylic and sulfonic acids of the aliphatic, cycloaliphatic, aromatic, aromatic-aliphatic and heterocyclic series, including saturated and unsaturated, mono-, di- and polybasic acids and/or those substituted in the usual manner, e.g., by alkyl, hydroxy, alkoxy, oxo, amino or one or more halogen atoms.

Examples of $R_1$ and $R_3$ acyl groups of alkanoic acids are the acyl radical of formic, acetic, propionic, butyric, isobutyric, valeric, isovaleric, caproic, enanthic, caprylic, pelargonic, capric, undecylic, lauric, tridecylic, myristic, pentadecylic, trimethylacetic, diethylacetic, tert.-butylacetic, $\beta$-cyclopentylpropionic, cyclohexylacetic and cyclohexanecarboxylic acids. Examples of contemplated equivalents are the acyl radicals of phenylacetic, phenoxyacetic, mono-, di- and trichloroacetic, aminoacetic, diethylaminoacetic, piperidinoacetic, morpholinoacetic, lactic, succinic, adipic, benzoic, nicotinic, isonicotinic and furan-2-carboxylic acids. Examples of acyl radicals of alkanesulfonic acids, particularly when $R_3$ is acyl, are the acyl radicals of methane-, ethane-, $\beta$-chloroethane-, propane-, isopropane-, butane-, cyclopentane- and cyclohexanesulfonic acids. Examples of contemplated equivalents are the acyl radicals of benzene-, p-toluene-, p-chlorobenzene- and sulfonic acids; as well as N,N-dimethyl-, diethyl-, bis($\beta$-chloroethyl)aminosulfonic acid, pyrrolidino-, piperidino-, piperazino-, N-methylpiperazino- and morpholinosulfonic acids.

The alkyl groups of the trialkylsilyl $R_1$ group each are of 1-4 carbon atoms, with trimethylsilyl being preferred.

Preferred acyl $R_4$ groups are alkanoyl of 2-8 carbon atoms, such as, for example, the acetyl, propionyl, butyryl, isobutyryl, valeryl, caproyl, heptanoyl and octanoyl.

Examples of $R_4$ alkyl groups are alkyl of 1-4 carbon atoms, especially the methyl and ethyl, and cycloalkyl of 3-8 carbon atoms, especially cyclopentyl.

The compounds of this invention possess valuable steroid homonal activity and are useful as pharmaceuticals. The invention accordingly also relates to the use of the compounds of the present invention as medicinal agents and/or in medicinal agents. The compounds of general Formula I are distinguished by strong progestational, ovulation-inhibiting and nidation-inhibiting activities. For example, 17$\alpha$-ethynyl-17$\beta$-hydroxy-18-methyl-4,15-estradien-3-one (A) is superior in the conventional Clauberg test to the known 17$\alpha$-ethynyl-17$\beta$-hydroxy-18-methyl-4-estren-3-one (B).

In the following table, the McPhail values are indicated after oral administration to infantile female rabbits.

TABLE

| Clauberg Test p. o. | | |
|---|---|---|
| Compound | Dosage (mg.) | McPhail |
| A 17$\alpha$-Ethynyl-17$\beta$- | 0.1 | 3.0 |
| hydroxy-18-methyl- | 0.03 | 2.5 |
| 4,15-estradien-3-one | 0.01 | 1.5 |
| B 17$\alpha$-Ethynyl-17$\beta$- | 0.1 | 1.8 |
| hydroxy-18-methyl- | 0.03 | 1.4 |
| 4-estren-3-one | 0.01 | 1.0 |

It can be seen from the McPhail values that the threshold dose (McPhail = 1.5) for the compound A of this invention and for the structurally similar compound B, is 0.01 mg. and 0.03–0.1 mg., respectively.

20°–200° C., it is also possible to simultaneously esterify the hydroxy groups at the 3- and 17-positions.

The reaction of the 3-ketone with a hydroxylamine salt to form a 3-oxime group is conducted in the presence of a base, for example, pyridine, collidine, sodium bicarbonate, sodium carbonate, sodium acetate or sodium hydroxide in an aqueous-alcoholic solution. Preferred salts of the hydroxylamine are the hydrochloride and the hydrogen sulfate. The reaction is conducted at temperatures of about 20° to 150° C.

The 3-oxime can be esterified or etherified in accordance with conventional methods. Esterification can be effected, for example, with the desired acid and/or the halogenide or anhydride of this acid in the presence of a tertiary amine, e.g., pyridine or collidine, at room temperature. Another suitable tertiary amine is 4-dimethylaminopyridine in pyridine. If the two free hydroxy groups of the 3-oxime-17-carbinol are to be esterified simultaneously, the reaction is conducted at temperatures of from 20° to 150° C., or the esterification can be accomplished with the desired acid in the presence of trifluoroacetic acid anhydride and/or the anhydride of the desired acid in the presence of a strong acid, e.g., trifluoroacetic acid, perchloric acid or p-toluenesulfonic acid.

The etherification of the 3-oxime with an alkyl or cycloalkyl group is preferably conducted with the corresponding alkyl or cycloalkyl halogenide in the presence of a strong base, e.g., sodium hydroxide solution, using a polar solvent, for example, hexamethylphosphoric triamide, at 0-30° C. or in the presence of a strong base, e.g., sodium hydride, and an ether, e.g., tetrahydrofuran, or a polar solvent, e.g., dimethyl sulfoxide, at 30°–100° C. The etherification of the 3-oxime can also be accomplished with a diazoalkane, particularly diazomethane.

The preparation of the 17-oxo steroids of general Formula II utilized as the starting compounds is illustrated by the following examples:

A. 15α-Hydroxy-18-methyl-4-estrene-3,17-dione

A 2-liter Erlenmeyer flask containing 500 ml. of a nutrient solution sterilized for 30 minutes at 120° C. in an autoclave and consisting of 3.0% glucose, 1.0% corn steep, 0.2% $NaNO_3$, 0.1% $KH_2PO_4$, 0.2% $K_2HPO_4$, 0.05% $MgSO_4$, 0.002% $FeSO_4$, and 0.05% KCl, is inoculated with a lyophilized culture of Penicillium raistrickii (ATCC 10 490) and shaken for 72 hours at 30° C. on a rotary shaker. Thereafter, a 20-liter glass fermentor filled with 15 liters of a medium having the same composition, sterilized at 121° C. and 1.1 atmospheres gauge, is inoculated with 250 ml. of this subculture. Under the addition of "Silicone SH" as a defrother, the germination is conducted at 29° C. under aeration (10 liters per minute), at 0.7 atmosphere gauge pressure, and under agitation (220 r.p.m.) for 24 hours. Under sterile conditions, 1.8 liters of the culture broth is transferred into 26 l. of a nutrient medium sterilized as above, having the same composition as the germination culture, and grown under the same conditions as the preliminary fermentation culture. After 12 hours, 2 l. of a sterilized suspension, ground extremely fine in the presence of aqueous "Tween" 80, of 120 g. of 18-methyl-4-estrene-3,17-dione in distilled water is added thereto and the germination is continued.

The progress of the germination is controlled by analysis by thin-layer chromatography of the methyl isobutyl ketone extracts of fermentor samples. After about 70 hours of contact time, the conversion is complete. The fungus mycelium is then filtered off, and the culture broth is extracted twice with respectively 20 l. of methyl isobutyl ketone. In parallel thereto, the filtered off mycelium is intensively agitated repeatedly with a mixture of methyl isobutyl ketone, acetone, and water, and extracted until a steroid substance is no longer detectable.

The organic extract solutions are combined and evaporated to dryness under vacuum at a bath temperature of 50° C. The brown crystalline residue is washed repeatedly with hexane to remove the silicone oil, dried, and finally, after treatment with activated carbon, recrystallized from ethyl acetate, thus obtaining 97.3 g. (76.5% of theory) of pure 15α-hydroxy-18-methyl-4-estrene-3,17-dione, m.p. 175°–177° C.

B. 15α-Hydroxy-18-methyl-3,3-(2',2'-dimethyl-1',3'-propylenedioxy)-5- and -5(10)-estren-17-one 20 g. of 15α-hydroxy-18-methyl-4-estrene-3,17-dione is agitated in 150 ml. of methylene chloride and 40 ml. of orthoformic acid triethyl ester with 60 g. of 2,2-dimethyl-1,3-propanediol and 200 mg. of p-toluenesulfonic acid for 20 hours at room temperature. The solution is diluted with ethyl acetate, neutralized with sodium bicarbonate solution, washed with water, dried over sodium sulfate, and concentrated under vacuum. The crude product is chromatographed on silica gel and with an acetonehexane gradient (0–20% acetone). With 20% acetone, 10.0 g. of 15α-hydroxy-3,3-(2',2'-dimethyl-1',3'-propylenedioxy)-18-methyl-5-estren-17-one is eluted, m.p. 206°–209° C. Furthermore, 15 g. of an oily mixture is obtained consisting, in a proportion of 1 : 1, of 15α-hydroxy-18-methyl-3,3-(2',2'-dimethyl-1',3'-propylenedioxy)-5-estren-17-one and 15α-hydroxy-18-methyl-3,3-(2',2'-dimethyl-1',3'-propylenedioxy)-5(10)-estren-17-one.

C. 15α-Mesyloxy-18-methyl-3,3-(2',2'-dimethyl-1',3'-propylenedioxy)-5- and -5(10)-estren-17-one Under ice cooling, 37 g. of 15α-hydroxy-18-methyl-3,3-(2',2'-dimethyl-1',3'-propylenedioxy)-5- and -5(10)-estren-17-one is combined in 370 ml. of pyridine with 27.1 ml. of methanesulfochloride and furthermore agitated for 3 hours at ice bath temperature. The mixture is then stirred into ice/water, the precipitate is vacuum-filtered, washed with water, taken up thereafter in methylene chloride, and dried, thus obtaining 40 g. of a mixture of 15α-mesyloxy-18-methyl-3,3-(2',2'-dimethyl-1',3'-propylenedioxy)-5- and -5(10)-estren-17-one in the form of an oil.

D. 18-Methyl-3,3-(2',2'-dimethyl-1',3'-propylenedioxy)-5- and -5(10),15-estradien-17-one 35 g. of 15α-mesyloxy-18-methyl-3,3-(2',2'-dimethyl-1',3'-propylenedioxy)-5- and -5(10)-estren-17-one is agitated in 350 ml. of dimethylformamide with 105 g. of anhydrous sodium acetate for 20 hours at room temperature. The mixture is then stirred into ice water, the thus-separated precipitate is vacuum-filtered, washed, and taken up in methylene chloride. After evaporation, 28.9 g. of crude 18-methyl-3,3-(2',2'-dimethyl-1',3'-propylenedioxy)-5- and -5(10),15-estradien-17-one is obtained.

E.
18-Methyl-3,3-(2',2'-dimethyl-1',3'-propylenedioxy)-15α-trimethylsilyloxy-5- and -5(10)-estren-17-one At room temperature, 10.0 g. of 15α-hydroxy-18-methyl-3,3-(2',2'-dimethyl-1',3'-propylenedioxy)-5- and -5(10)-estren-17-one is agitated in 40 ml. of pyridine with 10 ml. of trimethylchlorosilane for 4 hours. The solution is stirred into ice water, and the reaction product is extracted with methylene chloride. The solution is washed with water, dried over sodium sulfate, and evaporated to dryness under vacuum. The crude product is chromatographed on silica gel with 2.5–3.5% acetone-hexane, thus obtaining 3.2 g. of 18-methyl-3,3-(2',2'-dimethyl-1',3'-propylenedioxy)-15α-trimethylsilyloxy-5- and -5(10)-estren-17-one as an oily product.

F.
15α-Benzoyloxy-18-methyl-3,3-(2',2'-dimethyl-1',3'-propylenedioxy)-5- and -5(10)-estren-17-one In an ice bath, 10.0 g. of 15α-hydroxy-18-methyl-3,3-(2',2'-dimethyl-1',3'-propylenedioxy)-5- and -5(10)-estren-17-one in 25 ml. of pyridine is combined with 10 ml. of benzoyl chloride. The mixture is agitated at room temperature and introduced into ice/water after 4.5 hours. The reaction product is extracted with methylene chloride, washed with water, and dried over sodium sulfate. After chromatographing the crude product on silica gel with 2–3.5% acetone-hexane, 7.3 g. of 15α-benzoyloxy-18-methyl-3,3-(2',2'-dimethyl-1',3'-propylenedioxy)-5- and -5(10)-estren-17-one is obtained as a foamy compound.

G. 18-Methyl-15α-nitrooxy-4-estrene-3,17-dione

At −20° C., 6 ml. of concentrated nitric acid is added dropwise to 8.0 g. of 15α-hydroxy-18-methyl-4-estrene-3,17-dione in 60 ml. of acetic anhydride. After 1 hour, the reaction solution is introduced into ice/water. The thus-precipitated product is vacuum-filtered, washed several times with water, taken up in methylene chloride, and dried over sodium sulfate. After chromatographing the crude product on silica gel with acetone-hexane, 6.4 g. of 18-methyl-15α-nitrooxy-4-estrene-3,17-dione is produced.

H.
18-Methyl-15α-nitrooxy-3,3-(2',2'-dimethyl-1',3'-propylenedioxy-5- and -5(10)-estren-17-one At room temperature, 5.9 g. of 18-methyl-15α-nitrooxy-4-estrene-3,17-dione is agitated in 40 ml. of methylene chloride and 10 ml. of triethyl orthoformate with 18 g. of 2,2-dimethyl-1,3-propanediol and 50 mg. of p-toluenesulfonic acid for 3 hours, the solution diluted with ethyl acetate and worked up as described in Example B. After chromatographing the crude product with acetone-hexane, 4.7 g. of 18-methyl-15α-nitrooxy-3,3-(2',2'-dimethyl-1',3'-propylenedioxy)-5- and -5(10)-estren-17-one is obtained as an oily product.

I.
15α-Acetoxy-18-methyl-3,3-(2',2'-dimethyl-1',3'-propylenedioxy)-5 and -5(10)-estren-17-one In an ice bath, 12.0 g. of 15α-hydroxy-18-methyl-3,3-(2',2'-dimethyl-1',3'-propylenedioxy)-5 and -5(10)-estren-17-one in 30 ml. of pyridine is combined with 10 ml. of acetic anhydride. The mixture is agitated at room temperature and, after 3 hours, introduced into ice/water. The thus-precipitated product is vacuum-filtered, washed repeatedly with water, dried over sodium sulfate, and concentrated to dryness under vacuum, thus obtaining 9.7 g. of crude 15α-acetoxy-18-methyl-3,3-(2',2'-dimethyl-1',3'-propylenedioxy)-5 and -5(10)-estren-17-one as an oil.

J. 18-Methyl-3,3-(2',2'-dimethyl-1',3'-propylenedioxy)-5 and -5(10)-estradien-17-one Upon ice cooling and agitation, 100 ml. of methanesulfonic acid chloride is gradually added dropwise to 123 g. of 15α-hydroxy-18-methyl-3,3-(2',2'-dimethyl-1',3'-propylenedioxy)-5 and -5(10)-estren-17-one — prepared according to (B) — in 1 liter of pyridine. After 3.5 hours, 500 ml. of dimethylformamide and 317 g. of sodium acetate are added to the reaction mixture, and the latter is agitated for 24 hours at room temperature. The mixture is then introduced into ice water. The thus-precipitated product is vacuum-filtered, taken up in ethyl acetate, washed with water, and dried over sodium sulfate.

The crude product (103 g.) is chromatographed on silica gel with 10–14% acetone-hexane, thus obtaining 48.5 g. of 18-methyl-3,3-(2',2'-dimethyl-1',3'-propylenedioxy)-5 and -5(10),15-estradien-17-one.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

The temperatures in the following examples are set forth in degrees Celsius.

EXAMPLE 1

17α-Ethynyl-17β-hydroxy-18-methyl-4,15-estradien-3-one 7.5 g. of magnesium filings is reacted in 140 ml. of tetrahydrofuran with 24 ml. of ethyl bromide to obtain ethylmagnesium bromide. To this Grignard solution is added 300 ml. of tetrahydrofuran, and under ice cooling acetylene is passed through the solution for about 40 minutes. Then, a solution of 5 g. of 18-methyl-3,3-(2',2'-dimethyl-1',3'-propanediol)-5-and -5(10),15-estradien-17-one in 200 ml. of tetrahydrofuran is added dropwise to the reaction solution, and the latter is agitated at room temperature. After 2 hours, the solution is carefully combined with an ammonium chloride solution and diluted with ether. The organic phase is washed repeatedly with water, dried over sodium sulfate, and evaporated to dryness under vacuum. After chromatographing the crude product on silica gel with 2.5–2.9% acetone-hexane, the yield is 3.1 g. of 17α-ethynyl-18-methyl-3,3-(2',2'-dimethyl-1',3'-propylenedioxy)-5,15 and -5(10),15-estradien-17β-ol; these compounds are agitated under reflux in 70 ml. of methanol and 14 ml. of water with 2.3 g. of oxalic acid for 40 minutes. The solution is diluted with ether, washed neutral with water, dried, and treated with activated carbon. After recrystallization from acetone-hexane, 1.4 g. of 17α-ethynyl-17β-hydroxy-18-methyl-4,15-estradien-3-one is obtained; m.p. 197.9°.

EXAMPLE 2

17α-Ethynyl-17β-hydroxy-18-methyl-4,15-estradien-3-one 3.0 g. of magnesium filings is reacted in 56 ml. of tetrahydrofuran with 9.6 ml. of ethyl bromide to obtain ethylmagnesium bromide. The Grignard solution is diluted with 100 ml. of tetrahydrofuran and cooled to 0°. Acetylene is then introduced for 30 minutes, and thereafter a solution of 2.0 g. of 18-methyl-3,3-(2',2'-dimethyl-1',3'-propylenedioxy)-15α-trimethylsiloxy-5 and -5(10)-estren-17-one in 80 ml. of tetrahydrofuran is added dropwise thereto, and the mixture is agitated for 1 hour at room temperature. The solution is worked up as described in Example 1. The crude product is chromatographed on silica gel. With 3.5–4.5% acetone-hexane, 700 mg. of 17α-ethynyl-18-methyl-3,3-(2',2'-dimethyl-1',3'-propylenedioxy)-5(10),15-estradien-17β-ol [m.p. 223°–225° (Z)] is eluted which is agitated under reflux, as described in Example 1, with 500 mg. of oxalic acid in 12 ml. of methanol and 1.5 ml. of water for 15 minutes. The crude product is recrystallized from acetone/hexane. Yield: 510 mg. of 17α-ethynyl-17β-hydroxy-18-methyl-4,15-estradien-3-one, m.p. 190°–192°.

EXAMPLE 3

17α-Ethynyl-17β-hydroxy-18-methyl-4,15-estradien-3-one 5.0 g. of magnesium filings is reacted in 100 ml. of tetrahydrofuran with 18 ml. of ethyl bromide to obtain ethylmagnesium bromide. The solution is diluted with 100 ml. of tetrahydrofuran and cooled to 0°. Acetylene is introduced into the solution for 30 minutes, and then a solution of 4.5 g. of 15α-acetoxy-18-methyl-3,3-(2',2'-dimethyl-1',3'-propylenedioxy)-5- and -5(10)-estren-17-one in 80 ml. of tetrahydrofuran is added thereto. The mixture is agitated for 1 hour at room temperature and worked up as disclosed in Example 1. The thus-obtained crude 17α-ethynyl-18-methyl-3,3-(2',2'-dimethyl-1',3'-propylenedioxy)-5,15- and -5(10),15-estradien-17β-ol (3.7 g.) is agitated for 45 minutes under reflux in 70 ml. of methanol and 14 ml. of water with 2.5 g. of oxalic acid. The solution is diluted with ether, washed with water, and dried over sodium sulfate. The crude product is chromatographed on silica gel with acetone-hexane, thus obtaining 2.1 g. of 17α-ethynyl-17β-hydroxy-18-methyl-4,15-estradien-3-one; m.p. 189°–192°.

EXAMPLE 4

17β-Acetoxy-17α-ethynyl-18-methyl-4,15-estradien-3-one

A solution of 2.0 g. of 17α-ethynyl-17β-hydroxy-18-methyl-4,15-estradien-3-one in 40 ml. of collidine and 13 ml. of acetic anhydride is heated to boiling for 5 hours under nitrogen. After cooling, the solution is poured into ice/water. The reaction product is extracted with methylene chloride, washed in succession with 2N hydrochloric acid, sodium bicarbonate solution, and water, and dried over sodium sulfate. The crude product is chromatographed on silica gel. With 25–30% ethyl acetate-hexane, 950 mg. of 17β-acetoxy-17β-ethynyl-18-methyl-4,15-estradien-3-one is eluted which melts, after recrystallization from acetone/methanol, at 163°–164°.

EXAMPLE 5

17α-Ethynyl-17β-butyryloxy-18-methyl-4,15-estradien-3-one

Under nitrogen and refluxing, 500 mg. of 17α-ethynyl-17β-hydroxy-18-methyl-4,15-estradien-3-one is heated in 2 ml. of butyric acid anhydride and 2 ml. of collidine for 10 hours. The reaction mixture is worked up as described in Example 4. After chromatography of the crude product on silica gel with acetone-hexane, the yield is 310 mg. of 17α-ethynyl-17β-butyryloxy-18-methyl-4,15-estradien-3-one which melts, after recrystallization from acetone/methanol, at 160°–162°.

EXAMPLE 6

17α-Ethynyl-17β-heptanoyloxy-18-methyl-4,15-estradien-3-one

Under nitrogen, 300 mg. of 17α-ethynyl-17β-hydroxy-18-methyl-4,15-estradien-3-one is agitated at 170° for 17 hours in 2 ml. of enanthic acid anhydride and 2 ml. of collidine. The reaction product is worked up as set forth in Example 4. The excess enanthic acid, if any, is removed by steam distillation. The product obtained after ether extraction is chromatographed on silica gel with acetone-hexane, thus obtaining 175 mg. of 17α-ethynyl-17β-heptanoyloxy-18-methyl-4,15-estradien-3-one as an oil.

EXAMPLE 7

17α-Ethynyl-18-methyl-17β-octanoyloxy-4,15-estradien-3-one

From a solution of 3.5 ml. of caprylic acid anhydride in 250 ml. of benzene, 50 ml. is distilled off. After cooling to room temperature, the mixture is combined with 3.5 ml. of trifluoroacetic acid anhydride. After 30 minutes, 4.0 g. of 17α-ethynyl-17β-hydroxy-18-methyl-4,15-estradien-3-one is added thereto, and the mixture is agitated for another 2 hours. The reaction solution is mixed, under ice cooling, with 50 ml. of acetone/water (1 : 1), agitated for 30 minutes, and then concentrated under vacuum. The residue is taken up in methylene chloride, washed with sodium bicarbonate solution and water, and dried over sodium sulfate. The crude product is chromatographed of silica gel. With 14–18% ethyl acetate-hexane, 2.3 g. of 17α-ethynyl-18-methyl-17β-octanoyloxy-4,15-estradien-3-one is eluted in the form of an oil.

EXAMPLE 8

17α-Ethynyl-18-methyl-17β-undecanoyloxy-4,15-estradien-3-one

From a solution of 4.0 g. of undecylic acid in 300 ml. of benzene, 50 ml. is distilled off. After cooling to room temperature, the mixture is combined with 4.5 ml. of trifluoroacetic acid anhydride. After 30 minutes, 4.0 g. of 17α-ethynyl-17β-hydroxy-18-methyl-4,15-estradien-3-one is added thereto. The mixture is agitated for 2.5 hours, and the solution is worked up as described in Example 7. The crude product is chromatographed on silica gel with 18–25% ethyl acetate-hexane, thus obtaining 2.6 g. of 17α-ethynyl-18-methyl-17β-undecanoyloxy-4,15-estradien-3-one as an oil.

EXAMPLE 9

17α-Ethynyl-17β-hexadecanoyloxy-18-methyl-4,15-estradien-3-one

From a solution of 4.1 g. of palmitic acid in 200 ml. of benzene, 40 ml. are distilled off. After cooling to room temperature, the mixture is combined with 2.3 ml. of trifluoroacetic acid anhydride. After 30 minutes, 4.2 g. of 17α-ethynyl-17β-hydroxy-18-methyl-4,15-estradien-3-one is added thereto, and the mixture is stirred for another 2 hours. The reaction product is combined under ice cooling with 30 ml. of acetone/water (1 : 1), agitated for 30 minutes, and then evaporated to dryness under vacuum. The residue is taken up in methylene chloride and washed with 10 ml. of 10% sodium hydroxide solution. The thus-precipitated sodium palmitate is vacuum-filtered; the solution is washed neutral, dried, and concentrated under vacuum. The crude product is chromatographed on silica gel. With 12–16% ethyl acetate-hexane, 2.8 g. of 17α-ethynyl-17β-hexadecanoyloxy-18-methyl-4,15-estradien-3-one is eluted in the form of an oil.

EXAMPLE 10

17α-Ethynyl-17β-hydroxy-18-methyl-4,15-estradien-3-one

Acetylene is passed for about 45 minutes through a solution, cooled with ice water, of 100 ml. of n-butyllithium (approximately 15% strength in hexane) in 350 ml. of tetrahydrofuran. Thereafter, 10.0 g. of 18-methyl-3,3-(2',2'-dimethyl-1',3'-propylenedioxy)-5 and -5(10),15-estradien-17-one in 100 ml. of tetrahydrofuran is added dropwise thereto under agitation. After 30 minutes, the solution is combined with saturated ammonium chloride solution, diluted with ethyl acetate, washed neutral with water, and dried over sodium sulfate. The solution is concentrated to dryness under vacuum, thus obtaining 11.4 g. of crude 17α-ethynyl-18-methyl-3,3-(2',2'-dimethyl-1',3'-propylenedioxy)-5 and -5(10),15-estradien-17β-ol, which is suspended in 70 ml. of acetone. This reaction mixture is combined with 0.1 ml. of concentrated hydrochloric acid, stirred for 2 hours at room temperature, and then the solution is poured into ice water. The thus-precipitated product is vacuum-filtered, dissolved in ethyl acetate, and dried over sodium sulfate. After chromatographing the crude product on silica gel with 20% acetone-hexane, the product is 4.8 g. of 17α-ethynyl-17β-hydroxy-18-methyl-4,15-estradien-3-one, m.p. 199°–200°.

EXAMPLE 11

17β-Acetoxy-17α-ethynyl-18-methyl-4,15-estradien-3-one 40 ml. of acetic anhydride and 10 mg. of p-toluenesulfonic acid are added to 2.0 g. of 17α-ethynyl-17β-hydroxy-18-methyl-4,15-estradien-3-one in 20 ml. of methylene chloride. The solution is agitated under nitrogen for 6 hours at room temperature, then diluted with ethyl acetate, washed neutral with sodium bicarbonate solution, and dried over sodium sulfate. After chromatography on silica gel with 7–9% acetone-hexane, the yield is 560 mg. of 17β-acetoxy-17α-ethynyl-18-methyl-4,15-estradien-3-one; m.p. after recrystallization from acetone/hexane: 163°–164°.

The following compounds are obtained analogously: 17β-butyryloxy-, -heptanoyloxy-, octanoyloxy-, -undecanoyloxy-, and -hexadecanoyloxy-17α-ethynyl-18-methyl-4,15-estradien-3-one.

EXAMPLE 12

17α-Ethynyl-17β-trimethylsiloxy-18-methyl-4,15-estradien-3-one

Under ice cooling, 1.5 g. of 17α-ethynyl-17β-hydroxy-18-methyl-4,15-estradien-3-one in 30 ml. of pyridine is combined with 8 ml. of trimethylchlorosilane. After 3 hours, the reaction mixture is introduced into ice water. The thus-precipitated product is vacuum-filtered, dissolved in methylene chloride solution, washed with water, and dried over sodium sulfate. After treating the crude product in acetone with active carbon and recrystallizing the thus-obtained product from acetone/hexane, the yield is 1.18 g. of 17α-ethynyl-17β-trimethylsiloxy-18-methyl-4,15-estradien-3-one, m.p. 158°–159°.

EXAMPLE 13

17α-Ethynyl-18-methyl-4,15-estradiene-3β,17β-diol

A solution of 5.0 g. of lithium tri-(tert.-butoxy)-aluminum hydride in 30 ml. of tetrahydrofuran is added gradually to 2.0 g. of 17α-ethynyl-17β-hydroxy-18-methyl-4,15-estradien-3-one in 60 ml. of tetrahydrofuran; the mixture is agitated for 1 hour at room temperature under nitrogen. The solution is then stirred into ice water which contains sulfuric acid. The thus-precipitated product is filtered off, dissolved in ethyl acetate, washed with water, and dried over sodium sulfate. After chromatography of the crude product on silica gel with 10–13% acetone-hexane and recrystallization from aceton/hexane, the yield is 400 mg. of 17α-ethynyl-18-methyl-4,15-estradiene-3β,17β-diol; m.p. 143°–144°.

EXAMPLE 14

17β-Acetoxy-17α-ethynyl-18-methyl-4,15-estradien-3β-ol

Analogously to Example 13, 1.5 g. of 17β-acetoxy-17α-ethynyl-18-methyl-4,15-estradien-3-one in 40 ml. of tetrahydrofuran is reacted with 4.5 g. of lithium tri-(tert.butoxy)-aluminum hydride in 30 ml. of tetrahydrofuran. After 1 hour, the solution is introduced into ice water which contains sulfuric acid and worked up analogously to Example 13. After chromatography of the crude product on silica gel with 5–8% acetone-hexane, 530 mg. of 17β-acetoxy-17α-ethynyl-18-methyl-4,15-estradien-3β-ol is obtained.

EXAMPLE 15

17α-Ethynyl-18-methyl-17β-trimethylsiloxy-4,15-estradien-3β-ol

As described in Example 13, 2.0 g. of 17β-ethynyl-18-methyl-17β-trimethylsiloxy-4,15-estradien-3-one in 60 ml. of tetrahydrofuran is reacted with 5 g. of lithium tri-(tert.-butoxy)-aluminum hydride in 30 ml. of tetrahydrofuran. The solution is poured into ice water after 45 minutes and then worked up analogously to Example 13. After chromatography of the crude product on silica gel with 4–7% acetone-hexane, the yield is 960 mg. of 17α-ethynyl-18-methyl-17β-trimethylsiloxy-4,15-estradien-3β-ol.

EXAMPLE 16

3β-Acetoxy-17α-ethynyl-18-methyl-4,15-estradien-17β-ol

At room temperature, 230 mg. of 17α-ethynyl-18-methyl-4,15-estradiene-3β,17β-diol in 3 ml. of pyridine is agitated with 1.5 ml. of acetic anhydride for 2 hours. The solution is introduced into ice water, extracted with methylene chloride, washed in succession with dilute sulfuric acid and water, and dried over sodium sulfate. After purification of the crude product by preparative layer chromatography [system: ether/chloroform 8+2], the yield is 115 mg. of 3β-acetoxy-17α-ethynyl-18-methyl-4,15-estradien-17β-ol.

EXAMPLE 17

17α-Ethynyl-3β-heptanoyloxy-18-methyl-4,15-estradien-17β-ol

At room temperature, 800 mg. of 17α-ethynyl-18-methyl-4,15-estradiene-3β,17β-diol in 5 ml. of pyridine is agitated for 4 hours with 3 ml. of enanthic acid anhydride. The solution is diluted with benzene and subjected to a steam distillation. The reaction mixture is extracted from the aqueous distillation residue with methylene chloride. After chromatography of the crude product on silica gel with acetone-hexane, 210 mg. of 17α-ethynyl-3β-heptanoyloxy-18-methyl-4,15-estradien-17β-ol is obtained as an oily product.

EXAMPLE 18

17α-Ethynyl-3β-isopropylsulfonyloxy-18-methyl-4,15-estradien-17β-ol

A solution of 450 mg. of 17α-ethynyl-18-methyl-17β-trimethylsiloxy-4,15-estradien-3β-ol in 40 ml. of absolute benzene is combined at room temperature with 5 ml. of triethylamine and then, under vigorous agitation, with 2.5 ml. of isopropylsulfonic acid chloride. The mixture is agitated for 48 hours at room temperature, then poured into ice water, and extracted with ether. The ether phase is washed with water, dried over sodium sulfate, and evaporated. The thus-obtained crude 17α-ethynyl-3β-isopropylsulfonyloxy-18-methyl-17β-trimethylsiloxy-4,15-estradiene (430 mg.) is combined at room temperature with 50 ml. of hydrochloric methanol and stirred for 10 minutes at room temperature. The solution is neutralized with sodium bicarbonate solution and then concentrated under vacuum. The residue is taken up in methylene chloride, washed with water, and dried over sodium sulfate. After the crude product has been chromatographed on silica gel with acetone-hexane, 170 mg. of 17α-ethynyl-3β-isopropylsulfonyloxy-18-methyl-4,15-estradien-17β-ol is obtained.

EXAMPLE 19

17α-Ethynyl-18-methyl-3β,17β-diundecanoyloxy-4,15-estradiene

From a solution of 4.0 g. of undecylic acid in 300 ml. of benzene, 50 ml. is distilled off. After cooling to room temperature, the solution is combined with 4.5 ml. of trifluoroacetic acid. After 30 minutes, 3.2 g. of 17α-ethynyl-18-methyl-4,15-estradiene-3β,17β-diol is added thereto. The mixture is agitated for 2.5 hours, and the reaction solution is combined with 50 ml. of acetone/water (1 : 1). The mixture is stirred for 30 minutes and then concentrated under vacuum. The residue is taken up in methylene chloride, washed with sodium bicarbonate solution and water, and dried over sodium sulfate. After chromatographing the crude product on silica gel with 15–20% ethyl acetate-hexane, the yield is 1.3 g. of 17α-ethynyl-18-methyl-3β,17β-diundecanoyloxy-4,15-estradiene in the form of an oil.

EXAMPLE 20

17β-Acetoxy-17α-ethynyl-3β-heptanoyloxy-18-methyl-4,15-estradiene

At room temperature, 450 mg. of 17β-acetoxy-17α-ethynyl-18-methyl-4,15-estradien-3β-ol in 3 ml. of pyridine is agitated for 3 hours with 2.5 ml. of enanthic acid anhydride. The solution is diluted with benzene and worked up analogously to Example 17. After chromatography of the crude product on silica gel with acetone-hexane, the yield is 85 mg. of 17β-acetoxy-17α-ethynyl-3β-heptanoyloxy-18-methyl-4,15-estradiene as an oil.

EXAMPLE 21

17α-Ethynyl-3β,17β-dihexadecanoyloxy-18-methyl-4,15-estradiene

From a solution of 5 g. of palmitic acid in 250 ml. of benzene, 65 ml. is distilled off. After cooling to room temperature, 2.8 ml. of trifluoroacetic acid anhydride is dropped thereto, and after 30 minutes, 2.7 g. of 17α-ethynyl-18-methyl-4,15-estradiene-3β,17β-diol is added to the reaction mixture. After 5 hours, the mixture is combined under ice cooling with 35 ml. of acetone/water (1 : 1), stirred for 30 minutes, and then evaporated to dryness under vacuum. The residue is taken up in methylene chloride and washed with 10 ml. of 10% sodium hydroxide solution. The thus-obtained precipitate of palmitate is vacuum-filtered; the solution is washed neutral, dried, and concentrated under vacuum. The crude product is chromatographed on silica gel. With ethyl acetate-hexane, 820 mg. of 17α-ethynyl-3β,17β-dihexadecanoyloxy-18-methyl-4,15-estradiene is obtained.

EXAMPLE 22

17α-Ethynyl-18-methyl-3-oximino-4,15-estradien-17β-ol 2.0 g. of 17α-ethynyl-17β-hydroxy-18-methyl-4,15-estradien-3-one in 60 ml. of methanol and 2 ml. of water is combined with 1.0 g. of hydroxylamine hydrochloride and 1.0 g. of sodium bicarbonate. The reaction mixture is stirred for 2.5 hours at 65° and then concentrated under vacuum. The residue is taken up in ethyl acetate, washed with water, and dried over sodium sulfate. After chromatographing the crude product on silica gel with acetone-hexane, 350 mg. of 17α-ethynyl-18-methyl-3-oximino-4,15-estradien-17β-ol is obtained; m.p. 110°–112°.

EXAMPLE 23

17β-Acetoxy-17α-ethynyl-18-methyl-4,15-estradien-3-one Oxime

As described in Example 22, 2.4 g. of 17β-acetoxy-17α-ethynyl-18-methyl-4,15-estradien-3-one in 60 ml. of methanol and 2 ml. of water is reacted with 1.0 g. of hydroxylamine hydrochloride and 1.0 g. of sodium bicarbonate. After 1.5 hours, the reaction mixture is worked up analogously to Example 22. After the crude product has been chromatographed on silica gel with acetone-hexane, 760 mg. of 17β-acetoxy-17α-ethynyl-18-methyl-4,15-estradien-3-one oxime is obtained.

EXAMPLE 24

17α-Ethynyl-18-methyl-17β-undecanoyloxy-4,15-estradien-3-one Oxime 1.9 g. of 17α-ethynyl-18-methyl-17β-undecanoyloxy-4,15-estradien-3-one in 50 ml. of methanol and 1.5 ml. of water is reacted, as described in Example 22, with 1.0 g. of hydroxylamine hydrochloride and 1.0 g. of sodium bicarbonate. The reaction mixture is worked up after 2 hours in analogy to Example 22. The crude product is chromatographed on silica gel with acetone-hexane, thus obtaining 600 mg. of 17α-ethynyl-18-methyl-17β-undecanoyloxy-4,15-estradien-3-one oxime as an oil.

EXAMPLE 25

17α-Ethynyl-3-methoximino-18-methyl-4,15-estradien-17β-ol

Under ice cooling and introduction of nitrogen, 4.8 g. of 17α-ethynyl-18-methyl-3-oximino-4,15-estradien-17β-ol in 100 ml. of hexamethylphosphoric triamide is combined with 10 ml. of 25% strength sodium hydroxide solution and 10 ml. of methyl iodide. After 1 hour, the solution is introduced into ice/water containing hydrochloric acid. The reaction mixture is extracted with ether; the solution is washed neutral with water and dried over sodium sulfate. The crude product is chromatographed on silica gel with acetone-hexane, thus obtaining 700 mg. of 17α-ethynyl-3-methoximino-18-methyl-4,15-estradien-17β-ol; m.p. 149°–150°.

EXAMPLE 26

17α-Ethynyl-3-cyclopentyloximino-18-methyl-4,15-estradien-17β-ol

At room temperature and under nitrogen, 2.7 g. of 17α-ethynyl-18-methyl-3-oximino-4,15-estradien-17β-ol in 65 ml. of hexamethylphosphoric triamide is reacted with 7 ml. of 25% sodium hydroxide solution and 7 ml. of cyclopentyl bromide and, after 4 hours, worked up analogously to Example 25. The crude product is chromatographed on silica gel with acetone-hexane, thus producing 145 mg. of 17α-ethynyl-3-cyclopentyloximino-18-methyl-4,15-estradien-17β-ol.

EXAMPLE 27

3-Acetoximino-17α-ethynyl-18-methyl-4,15-estradien-17β-ol 250 mg. of 17α-ethynyl-18-methyl-3-oximino-4,15-estradien-17β-ol in 3 ml. of pyridine is agitated with 1.5 ml. of acetic anhydride for 1 hour at room temperature. The solution is introduced into ice/water, extracted with methylene chloride, washed in succession with dilute sulfuric acid and water, and dried over sodium sulfate. The crude product is purified by preparative layer chromatography (system ether/chloroform 8+2), thus obtaining 135 mg. of 3-acetoximino-17α-ethynyl-18-methyl-4,15-estradien-17β-ol.

EXAMPLE 28

17α-Ethynyl-3-isobutyryloximino-18-methyl-4,15-estradien-17β-ol

At room temperature, 380 mg. of 17α-ethynyl-18-methyl-3-oximino-4,15-estradien-17β-ol in 4 ml. of pyridine is stirred with 2 ml. of isobutyric acid anhydride for 30 minutes. After the reaction product has been worked up in accordance with Example 27 and chromatography of the crude product on silica gel with acetone-hexane, 170 mg. of 17α-ethynyl-3-isobutyryloximino-18-methyl-4,15-estradien-17β-ol is obtained.

EXAMPLE 29

17α-Ethynyl-3-heptanoyloximino-18-methyl-4,15-estradien-17β-ol

At room temperature, 700 mg. of 17α-ethynyl-18-methyl-3-oximino-4,15-estradien-17β-ol in 5 ml. of pyridine is agitated with 3 ml. of enanthic acid anhydride for 3 hours. The solution is diluted with benzene and subjected to a steam distillation. The reaction product is extracted from the aqueous remainder of the distillation with methylene chloride. After chromatographing the crude product on silica gel with acetone-hexane, 190 mg. of 17α-ethynyl-3-heptanoyloximino-18-methyl-4,15-estradien-17β-ol is obtained as an oily product.

EXAMPLE 30

17β-Acetoxy-3-acetoximino-17α-ethynyl-18-methyl-4,15-estradiene

At room temperature, 460 mg. of 17β-acetoxy-17α-ethynyl-18-methyl-4,15-estradien-3-one oxime in 5 ml. of pyridine is agitated with 2 ml. of acetic anhydride for 1 hour. The solution is introduced into ice/water and worked up as described in Example 27. The crude product is chromatographed on silica gel with acetone-hexane, yielding 290 mg. of 17β-acetoxy-3-acetoximino-17α-ethynyl-18-methyl-4,15-estradiene.

EXAMPLE 31

17β-Acetoxy-17α-ethynyl-3-isobutyryloximino-18-methyl-4,15-estradiene

At room temperature, 400 mg. of 17β-acetoxy-17α-ethynyl-18-methyl-4,15-estradien-3-one oxime in 4 ml. of pyridine is agitated with 2 ml. of isobutyric acid anhydride for 30 minutes. After the reaction mixture has been worked up as disclosed in Example 27 and the crude product has been chromatographed on silica gel, 180 mg. of 17β-acetoxy-17α-ethynyl-3-isobutyryloximino-18-methyl-4,15-estradiene is obtained.

EXAMPLE 32

17β-Acetoxy-17α-ethynyl-3-heptanoyloximino-18-methyl-4,15-estradiene

At room temperature, 800 mg. of 17β-acetoxy-17α-ethynyl-18-methyl-4,15-estradien-3-one oxime in 6 ml. of pyridine is agitated for 2.5 hours with 3.5 ml. of enanthic acid anhydride. The solution is diluted with benzene and worked up analogously to Example 29. After chromatographing the crude product on silica gel with acetone-hexane, 380 mg. of 17β-acetoxy-17α-ethynyl-3-heptanoyloximino-18-methyl-4,15-estradiene is obtained.

EXAMPLE 33

17β-Acetoxy-17α-ethynyl-3-methoximino-18-methyl-4,15-estradiene

Analogously to Example 25, 1.3 g. of 17β-acetoxy-17α-ethynyl-18-methyl-4,15-estradien-3-one oxime in 30 ml. of hexamethylphosphoric triamide is reacted with 3.5 ml. of 25% sodium hydroxide solution and 3.5 ml. of methyl iodide. After 1.5 hours, the solution is introduced into ice/water which contains hydrochloric acid and worked up analogously to Example 25. The crude product is chromatographed on silica gel with acetone-hexane, thus obtaining 580 mg. of 17β-acetoxy-17α-ethynyl-3-methoximino-18-methyl-4,15-estradiene.

EXAMPLE 34

3-Acetoximino-17α-ethynyl-17β-butyryloxy-18-methyl-4,15-estradiene

At room temperature, 500 mg. of 17α-ethynyl-17β-butyryloxy-18-methyl-4,15-estradien-3-one oxime in 5 ml. of pyridine is agitated for 1 hour with 25 ml. of acetic anhydride. The solution is introduced into ice/water and worked up as described in Example 27. After the crude product has been chromatographed on silica gel with acetone-hexane, 370 mg. of 3-acetoximino-17α-ethynyl-17β-butyryloxy-18-methyl-4,15-estradiene is obtained.

EXAMPLE 35

17α-Chloroethynyl-17β-hydroxy-18-methyl-4,15-estradien-3-one

Under argon, 32 ml. of a 2-molar ethereal methyllithium solution is added at room temperature to 2.3 ml. of 1,2-dichloroethylene in 40 ml. of absolute ether. After 30 minutes, 2.0 g. of 18-methyl-3,3-(2',2'-dimethyl-1',3'-propylenedioxy)-5 and -5(10),15-estradien-17-one in 70 ml. of tetrahydrofuran is added dropwise thereto, and the reaction mixture is stirred for 1.5 hours at 60°. After cooling, the solution is gently combined with saturated ammonium chloride solution, diluted with ether, washed neutral with water, and dried over sodium sulfate. The crude product is chromatographed on silica gel with acetone-hexane, thus obtaining 1.2 g. of 17α-chloroethynyl-3,3-(2',2'-dimethyl-1',3'-propylenedioxy)-18-methyl-5 and 5(10),15-estradien-17β-ol; these compounds are agitated in 10 ml. of methanol and 1 ml. of water with 400 mg. of oxalic acid for 4 hours at 65°. The solution is neutralized with sodium bicarbonate solution and concentrated under vacuum. The residue is dissolved in ethyl acetate, washed with water, and dried over sodium sulfate. After purification by preparative layer chromatography (system: ether/chloroform 8+2) and recrystallization from acetone/hexane, 170 mg. of 17α-chloroethynyl-17β-hydroxy-18-methyl-4,15-estradien-3-one is obtained; m.p. 153°–154°.

EXAMPLE 36

17β-Acetoxy-17α-chloroethynyl-18-methyl-4,15-estradien-3-one

Under nitrogen, 1.0 g. of 17α-chloroethynyl-17β-hydroxy-18-methyl-4,15-estradien-3-one is agitated at room temperature in 10 ml. of pyridine with 5 ml. of acetic anhydride and 50 mg. of 4-(dimethylamino)-pyridine for 4 hours. The solution is introduced into ice/water which contains sulfuric acid. The thus-precipitated product is vacuum-filtered, dissolved in methylene chloride, washed with water, and dried over sodium sulfate. After chromatographing the crude product on silica gel with acetone-hexane, 760 mg. of 17β-acetoxy-17α-chloroethynyl-18-methyl-4,15-estradien-3-one is obtained.

EXAMPLE 37

17β-Butyryloxy-17α-chloroethynyl-18-methyl-4,15-estradien-3-one

At room temperature, 400 mg. of 17α-chloroethynyl-17β-hydroxy-18-methyl-4,15-estradien-3-one in 4 ml. of pyridine is agitated for 8 hours with 2 ml. of butyric acid anhydride and 20 mg. of 4-(dimethylamino)-pyridine. The reaction product is introduced into ice/water which contains sulfuric acid and worked up as described in Example 36. After the crude product has been chromatographed on silica gel with acetone-hexane, 220 mg. of 17β-butyryloxy-17α-chloroethynyl-18-methyl-4,15-estradien-3-one is obtained.

EXAMPLE 38

17α-Chloroethynyl-18-methyl-17β-undecanoyloxy-4,15-estradien-3-one

From a solution of 3.5 g. of undecylic acid in 300 ml. of benzene, 70 ml. is distilled off. After cooling to room temperature, the solution is combined with 4 ml. of trifluoroacetic acid anhydride. After 30 minutes, 3.2 of 17α-chloroethynyl-17β-hydroxy-18-methyl-4,15-estradien-3-one is added thereto. The mixture is agitated for 2.5 hours. Under ice cooling, the mixture is then combined with 50 ml. of acetone/water (1 : 1), stirred for 30 minutes, and then concentrated under vacuum. The residue is taken up in methylene chloride, washed with sodium bicarbonate solution and water, and dried over sodium sulfate. The crude product is chromatographed on silica gel. With ethyl acetate-hexane, 1.1 g. of 17α-chloroethynyl-18-methyl-17β-undecanoyloxy-4,15-estradien-3-one is obtained as an oil.

EXAMPLE 39

17α-Chloroethynyl-18-methyl-4,15-estradiene-3β,17β-diol

A solution of 3.0 g. of lithium tri-(tert.-butoxy)-aluminum hydride in 25 ml. of tetrahydrofuran is added gradually to 1.2 g. of 17α-chloroethynyl-17β-hydroxy-18-methyl-4,15-estradien-3-one in 30 ml. of tetrahydrofuran, and the mixture is agitated for 1 hour at room temperature under nitrogen. The solution is stirred into ice/water which contains sulfuric acid. The thus-precipitated product is filtered off, dissolved in ethyl acetate, washed with water, and dried over sodium sulfate. After chromatography of the crude product on silica gel with acetone-hexane, 380 mg. of 17α-chloroethynyl-18-methyl-4,15-estradiene-3β,17β-diol is obtained.

EXAMPLE 40

17β-Acetoxy-17α-chloroethynyl-18-methyl-4,15-estradien-3β-ol

As described in Example 39, 900 mg. of 17β-acetoxy-17α-ethynyl-18-methyl-4,15-estradien-3-one in 25 ml. of tetrahydrofuran is reacted with 2.3 g. of lithium tri-(tert.-butoxy)-aluminum hydride in 20 ml. of tetrahydrofuran. After one hour, the solution is introduced into ice/water which contains sulfuric acid and worked up analogously to Example 39. After purification of the crude product by preparative layer chromatography (system: ether/chloroform 8+2), 410 mg. of 17β-acetoxy-17α-chloroethynyl-18-methyl-4,15-estradien-3β-ol is obtained.

EXAMPLE 41

17β-Acetoxy-17α-chloroethynyl-3β-heptanoyloxy-18-methyl-4,15-estradiene

At room temperature, 400 mg. of 17β-acetoxy-17α-ethynyl-18-methyl-4,15-estradien-3β-ol in 3 ml. of pyridine is agitated for 3 hours with 2.5 ml. of enanthic acid anhydride. The solution is diluted with benzene and subjected to a steam distillation. The reaction product is extracted from the aqueous residue of the distillation with methylene chloride. After chromatographing the crude product on silica gel with acetone-hexane, 170 mg. of 17β-acetoxy-17α-chloroethynyl-3β-heptanoyloxy-18-methyl-4,15-estradiene is obtained.

EXAMPLE 42

17β-Chloroethynyl-18-methyl-3-oximino-4,15-estradien-17β-ol 1.0 g. of hydroxylamine hydrochloride and 1.0 g. of sodium bicarbonate are added to 2.3 g. of 17α-chloroethynyl-17β-hydroxy-18-methyl-4,15-estradien-3-one in 60 ml. of methanol and 2 ml. of water. The reaction mixture is agitated for 3 hours at 65° and then concentrated under vacuum. The residue is taken up in ethyl acetate, washed with water, and dried over sodium sulfate. After chromatographing the crude product on silica gel with acetone-hexane, 1.4 g. of 17α-chloroethynyl-18-methyl-3-oximino-4,15-estradien-17β-ol is obtained.

EXAMPLE 43

17β-Acetoxy-17α-chloroethynyl-18-methyl-4,15-estradien-3-one Oxime

As described in Example 42, 1.2 g. of 17β-acetoxy-17α-chloroethynyl-18-methyl-4,15-estradien-3-one in 35 ml. of methanol and 1.2 ml. of water is reacted with 600 mg. of hydroxylamine hydrochloride and 700 mg. of sodium bicarbonate. After one hour, the reaction mixture is worked up analogously to Example 42. After the crude product has been chromatographed on silica gel with acetone-hexane, 750 mg. of 17β-acetoxy-17α-chloroethynyl-18-methyl-4,15-estradien-3-one oxime is obtained.

EXAMPLE 44

17α-Chloroethynyl-3-heptanoyloximino-18-methyl-4,15-estradien-17β-ol

At room temperature, 850 mg. of 17α-chloroethynyl-18-methyl-3-oximino-4,15-estradien-17β-ol in 6 ml. of pyridine is agitated for 3 hours with 3.5 ml. of enanthic acid anhydride. The solution is diluted with benzene and subjected to a steam distillation. The reaction product is extracted from the aqueous distillation residue with methylene chloride. After chromatographing the crude product on silica gel with acetonehexane, 210 mg. of 17α-chloroethynyl-3-heptanoyloximino-18-methyl-4,15-estradien-17β-ol is produced.

EXAMPLE 45

17α-Chloroethynyl-3-methoximino-18-methyl-4,15-estradien-17β-ol

Under ice cooling and introduction of nitrogen, 2.6 g. of 17α-chloroethynyl-18-methyl-3-oximino-4,15-estradien-17β-ol in 50 ml. of hexamethylphosphoric triamide is combined with 2 ml. of 25% sodium hydroxide solution and 5 ml. of methyl iodide. After one hour, the solution is introduced into ice/water which contains hydrochloric acid. The mixture is extracted with ether, the solution washed neutral with water and dried over sodium sulfate. The crude product is chromatographed on silica gel with acetone-hexane, thus obtaining 510 mg. of 17α-chloroethynyl-3-methoximino-18-methyl-4,15-estradien-17β-ol.

EXAMPLE 46

17β-Hydroxy-18-methyl-17α-propin-1-yl-4,15-estradien-3-one

Methylacetylene is passed for about 30 minutes through a solution, cooled with ice/water, of 60 ml. of n-butyllithium (15% strength in hexane) in 250 ml. of tetrahydrofuran. Thereafter, 5.8 g. of 18-methyl-3,3-(2′,2′-dimethyl-1′,3′-propylenedioxy)-5 and -5(10),15-estradien-17-one in 60 ml. of tetrahydrofuran is added dropwise thereto under agitation. After 2 hours, the solution is gently combined with saturated ammonium chloride solution, diluted with ethyl acetate, washed neutral with water, and dried over sodium sulfate. The solution is evaporated to dryness under vacuum, thus obtaining 4.6 g. of crude 18-methyl-3,3-(2′,2′-dimethyl-1′,3′-propylenedioxy)-17α-propin-1-yl-5 and -5(10),15-estradien-17β-ol; these compounds are suspended in 50 ml. of acetone and combined at room temperature with 0.1 ml. of concentrated hydrochloric acid. After one hour, the solution is introduced into ice/water. The thus-precipitated product is vacuum-filtered, dissolved in ethyl acetate, and dried over sodium sulfate. The crude product is chromatographed on silica gel with acetone-hexane, thus obtaining 1.8 g. of 17β-hydroxy-18-methyl-17α-propin-1-yl-4,15-estradien-3-one.

EXAMPLE 47

17β-Acetoxy-18-methyl-17α-propin-1-yl-4,15-estradien-3-one

Under nitrogen, 250 mg. of 17β-hydroxy-18-methyl-17α-propinyl-4,15-estradien-3-one in 2.5 ml. of pyridine is agitated at room temperature for 2 hours with 1 ml. of acetic anhydride and 10 mg. of 4-(dimethylamino)-pyridine. After the reaction mixture has been worked up as described in Example 36, and after the crude product has been chromatographed on silica gel with acetone-hexane, 110 mg. of 17β-acetoxy-18-methyl-17α-propin-1-yl-4,15-estradien-3-one is obtained.

EXAMPLE 48

18-Methyl-17α-propin-1-yl-4,15-estradiene-3β,17β-diol

As described in Example 39, 800 mg. of 17β-hydroxy-18-methyl-17α-propin-1-yl-4,15-estradien-3-one in 25 ml. of tetrahydrofuran is reacted with 1.4 g. of lithium tri-(tert.-butoxy)-aluminum hydride in 15 ml. of tetrahydrofuran. After 1 hour, the solution is introduced into ice/water which contains sulfuric acid and worked up analogously to Example 39. After chromatography of the crude product on silica gel with acetone-hexane, the yield is 250 mg. of 18-methyl-17α-propin-1-yl-4,15-estradiene-3β,17β-diol.

EXAMPLE 49

18-Methyl-3-oximino-17α-propin-1-yl-4,15-estradien-17β-ol 1.2 g. of 17β-hydroxy-18-methyl-17α-propin-1-yl-4,15-estradien-3-one in 30 ml. of methanol and 1 ml. of water is stirred with 800 mg. of hydroxylamine hydrochloride and 800 mg. of sodium bicarbonate for 3 hours at 65° C. The reaction mixture is concentrated under vacuum. The residue is dissolved in ethyl acetate, washed with water, and dried over sodium sulfate. After the crude product has been chromatographed on silica gel with acetone-hexane, 430 mg. of 18-methyl-3- oximino-17α-propin-1-yl-4,15-estradien-17β-ol is obtained.

EXAMPLE 50

17β-Acetoxy-18-methyl-17α-propin-1-yl-4,15-estradien-3-one Oxime

As described in Example 49, 700 mg. of 17β-acetoxy-18-methyl-17α-propin-1-yl-4,15-estradien-3-one in 30 ml. of methanol and 1 ml. of water is reacted with 600 mg. of hydroxylamine hydrochloride and 700 mg. of sodium bicarbonate. After one hour, the reaction mixture is worked up analogously to Example 49. The crude product is chromatographed on silica gel with acetone-hexane, thus obtaining 240 mg. of 17β-acetoxy-18-methyl-17α-propin-1-yl-4,15-estradien-3-one oxime.

EXAMPLE 51

3-Cyclopentyloximino-18-methyl-17β-propin-1-yl-4,15-estradien-17β-ol

At room temperature, 1.1 g. of 18-methyl-3-oximino-17α-propin-1-yl-4,15-estradien-17β-ol in 30 ml. of hexamethylphosphoric triamide is reacted under nitrogen with 3 ml. of 25% sodium hydroxide solution and 3 ml. of cyclopentyl bromide. The reaction mixture is worked up after 4 hours analogously to Example 45. The crude product is chromatographed on silica gel with acetone-hexane, thus obtaining 115 mg. of 3-cyclopentyloximino-18-methyl-17α-propin-1-yl-4,15-estradien-17β-ol.

EXAMPLE 52

| Tablet Composition | |
|---|---|
| 0.050 mg. | 17α-ethynyl-17β-hydroxy-18-methyl-4,15-estradien-3-one |
| 0.050 mg. | 17α-ethynylestradiol |
| 109.900 mg. | lactose (DAB 6) [German Pharmacopoeia] |
| 8.000 mg. | corn starch (USP XVI) |
| 1.000 mg. | magnesium stearate (USP XVI) |
| 1.000 mg. | talc |
| 120.000 mg. | total weight of the tablet |

EXAMPLE 53

| Dragee Composition | |
|---|---|
| 0.030 mg. | α-ethynyl-17β-hydroxy-18-methyl-4,15-estradien-3-one |
| 0.050 mg. | 17α-ethynylestradiol |
| 31.920 mg. | lactose |
| 18.425 mg. | corn starch |
| 2.060 mg. | polyvinylpyrrolidone 25 |
| 0.010 mg. | methyl p-hydroxybenzoate [methylparaben] |
| 0.005 mg. | propyl p-hydroxybenzoate [propylparaben] |
| 2.500 mg. | talc |
| 55.000 mg. | total weight of the tablet which is made into a dragee with a weight of about 90 mg. with | the usual sugar mixture

EXAMPLE 54

| Dragee Composition | |
|---|---|
| 0.030 mg. | 17α-ethynyl-17β-hydroxy-1-methyl-4,15-estradien-3-one |
| 0.030 mg. | 17α-ethynylestradiol |
| 31.938 mg. | lactose |
| 18.425 mg. | corn starch |
| 2.060 mg. | polyvinylpyrrolidone 25 |
| 0.011 mg. | methyl p-hydroxybenzoate |
| 0.006 mg. | propyl p-hydroxybenzoate |

| Dragee Composition | |
|---|---|
| 2.500 mg. | talc |
| 55.000 mg. | total weight of the tablet which is made into a 90 mg. dragee with the usual sugar mixture |

EXAMPLE 55

| Tablet Composition | |
|---|---|
| 0.030 mg. | 17 α-ethynyl-17βhydroxy-18-methyl-4,15-estradien-3-one |
| 63.670 mg. | lactose |
| 15.000 mg. | microcrystalline cellulose |
| 1.000 mg. | talc |
| 0.300 mg. | magnesium stearate |
| 80.000 mg. | total weight of the tablet. |

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A $\Delta^{15}$-steroid of the formula

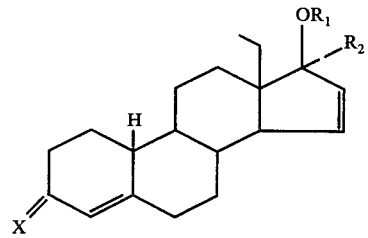

wherein $R_1$ is a hydrogen atom, trialkylsilyl wherein each alkyl is of 1–4 carbon atoms, or alkanoyl or alkanesulfonyl of 1–16 carbon atoms; $R_2$ is ethynyl, chloroethynyl or propinyl; and X is an oxygen atom,

or $NOR_4$, wherein $R_3$ is a hydrogen atom, alkanoyl or alkanesulfonyl of 1–16 carbon atoms, and $R_4$ is a hydrogen atom, alkanoyl of 2–8 carbon atoms, alkyl of 1–4 carbon atoms or cycloalkyl of 3–8 carbon atoms.

2. 17α-Ethynyl-17β-hydroxy-18-methyl-4,15-estradien-3-one, a compound of claim 1.

3. 17β-Acetoxy-17α-ethynyl-18-methyl-4,15-estradien-3-one, a compound of claim 1.

4. 17α-Ethynyl-17β-butyryloxy-18-methyl-4,15-estradien-3-one, a compound of claim 1.

5. 17α-Ethynyl-17β-heptanoyloxy-18-methyl-4,15-estradien-3-one, a compound of claim 1.

6. 17α-Ethynyl-18-methyl-17β-octanoyloxy-4,15-estradien-3-one, a compound of claim 1.

7. 17α-Ethynyl-18-methyl-17β-undecanoyloxy-4,15-estradien-3-one, a compound of claim 1.

8. 17α-Ethynyl-17β-hexadecanoyloxy-18-methyl-4,15-estradien-3-one, a compound of claim 1.

9. 17α-Ethynyl-17β-trimethylsiloxy-18-methyl-4,15-estradien-3-one, a compound of claim 1.

10. 17α-Ethynyl-18-methyl-4,15-estradiene-3β,17β-diol, a compound of claim 1.

11. 17β-Acetoxy-17α-ethynyl-18-methyl-4,15-estradien-3β-ol, a compound of claim 1.

12. 17α-Ethynyl-18-methyl-17β-trimethylsiloxy-4,15-estradien-3β-ol, a compound of claim 1.

13. 3β-Acetoxy-17α-ethynyl-18-methyl-4,15-estradien-17β-ol, a compound of claim 1.

14. 17α-Ethynyl-3β-heptanoyloxy-18-methyl-4,15-estradien-17β-ol, a compound of claim 1.

15. 17α-Ethynyl-3β-isopropylsulfonyloxy-18-methyl-4,15-estradien-17β-ol, a compound of claim 1.

16. 17α-Ethynyl-18-methyl-3β,17β-diundecanoyloxy-4,15-estradiene, a compound of claim 1.

17. 17β-Acetoxy-17α-ethynyl-3β-heptanoyloxy-18-methyl-4,15-estradiene, a compound of claim 1.

18. 17α-Ethynyl-3β,17β-dihexadecanoyloxy-18-methyl-4,15-estradiene, a compound of claim 1.

19. 17α-Ethynyl-18-methyl-3-oximino-4,15-estradien-17β-ol, a compound of claim 1.

20. 17β-Acetoxy-17α-ethynyl-18-methyl-4,15-estradien-3-one oxime, a compound of claim 1.

21. 17α-Ethynyl-18-methyl-17β-undecanoyloxy-4,15-estradien-3-one oxime, a compound of claim 1.

22. 17α-Ethynyl-3-methoximino-18-methyl-4,15-estradien-17β-ol, a compound of claim 1.

23. 17α-Ethynyl-3-cyclopentyloximino-18-methyl-4,15-estradien-17β-ol, a compound of claim 1.

24. 3-Acetoximino-17α-ethynyl-18-methyl-4,15-estradien-17β-ol, a compound of claim 1.

25. 17α-Ethynyl-3-isobutyryloximino-18-methyl-4,15-estradien-17β-ol, a compound of claim 1.

26. 17α-Ethynyl-3-heptanoyloximino-18-methyl-4,15-estradien-17β-ol, a compound of claim 1.

27. 17β-Acetoxy-3-acetoximino-17α-ethynyl-18-methyl-4,15-estradiene, a compound of claim 1.

28. 17β-Acetoxy-17α-ethynyl-3-isobutyryloximino-18-methyl-4,15-estradiene, a compound of claim 1.

29. 17β-Acetoxy-17α-ethynyl-3-heptanoyloximino-18-methyl-4,15-estradiene, a compound of claim 1.

30. 17β-Acetoxy-17α-ethynyl-3-methoximino-18-methyl-4,15-estradiene, a compound of claim 1.

31. 3-Acetoximino-17α-ethynyl-17β-butyryloxy-18-methyl-4,15-estradiene, a compound of claim 1.

32. 17α-Chloroethynyl-17β-hydroxy-18-methyl-4,15-estradien-3-one, a compound of claim 1.

33. 17β-Acetoxy-17α-chloroethynyl-18-methyl-4,15-estradien-3-one, a compound of claim 1.

34. 17β-Butyryloxy-17α-chloroethynyl-18-methyl-4,15-estradien-3-one, a compound of claim 1.

35. 17α-Chloroethynyl-18-methyl-17β-undecanoyloxy-4,15-estradien-3-one, a compound of claim 1.

36. 17α-Chloroethynyl-18-methyl-4,15-estradiene-3β,17β-diol, a compound of claim 1.

37. 17β-Acetoxy-17α-chloroethynyl-18-methyl-4,15-estradien-3β-ol, a compound of claim 1.

38. 17β-Acetoxy-17α-chloroethynyl-3β-heptanoyloxy-18-methyl-4,15-estradiene, a compound of claim 1.

39. 17α-Chloroethynyl-18-methyl-3-oximino-4,15-estradien-17β-ol, a compound of claim 1.

40. 17β-Acetoxy-17α-chloroethynyl-18-methyl-4,15-estradien-3-one oxime, a compound of claim 1.

41. 17α-Chloroethynyl-3-heptanoyloximino-18-methyl-4,15-estradien-17β-ol, a compound of claim 1.

42. 17α-Chloroethynyl-3-methoximino-18-methyl-4,15-estradien-17β-ol, a compound of claim 1.

43. 17β-Hydroxy-18-methyl-17α-propin-1-yl-4,15-estradien-3-one, a compound of claim 1.

44. 17β-Acetoxy-18-methyl-17α-propin-1-yl-4,15-estradien-3-one, a compound of claim 1.

45. 18-Methyl-17α-propin-1-yl-4,15-estradiene-3β,17β-diol, a compound of claim 1.

46. 18-Methyl-3-oximino-17α-propin-1-yl-4,15-estradien-17β-ol, a compound of claim 1.

47. 17β-Acetoxy-18-methyl-17α-propin-1-yl-4,15-estradien-3-one oxime, a compound of claim 1.

48. 3-Cyclopentyloximino-18-methyl-17α-propin-1-yl-4,15-estradien-17β-ol, a compound of claim 1.

49. A compound of claim 1 wherein X is an oxygen atom.

50. A compound of claim 49 wherein $R_1$ is a hydrogen atom or alkanoyl of 2-11 carbon atoms.

51. A compound of claim 50 wherein $R_2$ is ethinyl.

52. A pharmaceutical composition comprising a progestationally effective amount per unit dosage of a compound of claim 1, in admixture with a pharmaceutically acceptable carrier.

53. A composition of claim 52 adapted for oral ingestion and consisting essentially of 17α-ethynylestradiol.

* * * * *